US009782071B2

(12) United States Patent
Fujiu

(10) Patent No.: US 9,782,071 B2
(45) Date of Patent: Oct. 10, 2017

(54) OPHTHALMOLOGIC PHOTOGRAPHING APPARATUS AND OPHTHALMOLOGIC PHOTOGRAPHING METHOD

(71) Applicant: NIDEK CO., LTD., Aichi (JP)

(72) Inventor: Kenshiro Fujiu, Aichi (JP)

(73) Assignee: NIDEK CO., LTD., Aichi (JP)

( * ) Notice: Subject to any disclaimer, the term of this patent is extended or adjusted under 35 U.S.C. 154(b) by 328 days.

(21) Appl. No.: 14/064,477

(22) Filed: Oct. 28, 2013

(65) Prior Publication Data
US 2014/0118694 A1 May 1, 2014

(30) Foreign Application Priority Data
Oct. 31, 2012 (JP) .................................. 2012-241327

(51) Int. Cl.
*A61B 3/14* (2006.01)
*A61B 3/10* (2006.01)
(Continued)

(52) U.S. Cl.
CPC .............. *A61B 3/14* (2013.01); *A61B 3/0058* (2013.01); *A61B 3/102* (2013.01); *A61B 3/1025* (2013.01); *A61B 3/1225* (2013.01)

(58) Field of Classification Search
USPC ........ 351/200, 205, 206, 209–211, 221, 222, 351/224, 223, 243–246
See application file for complete search history.

(56) References Cited

U.S. PATENT DOCUMENTS 8,419,186 B2    4/2013 Isogai
2006/0228011 A1 10/2006 Everett et al.
(Continued)

FOREIGN PATENT DOCUMENTS

EP    1872713 A1    1/2008
EP    2147634       1/2010
(Continued)

OTHER PUBLICATIONS

Extended European Search Report dated Feb. 6, 2014 filed in corresponding European patent application No. 13190895.6.
(Continued)

*Primary Examiner* — Brandi Thomas
(74) *Attorney, Agent, or Firm* — Rankin, Hill & Clark LLP

(57) ABSTRACT

An ophthalmologic photographing apparatus includes: a photographing optical system including an optical scanner for scanning an examinee's eye with measurement light and a detector for detecting a coherent state of reflected light of the measurement light from the examinee's eye and reference light, the photographing optical system being configured to capture a tomographic image of the examinee's eye in response to an output signal from the detector; a reference data setting unit for setting a photographing condition of a previously acquired captured image as reference data for a follow-up; an image capture data setting unit for setting the reference data set by the reference data setting unit as image capture data for the follow-up; and a tomographic image acquisition controller for acquiring a tomographic image of the examinee's eye by controlling the photographing optical system based on the reference data set as the image capture data.

20 Claims, 6 Drawing Sheets

(51) Int. Cl.
*A61B 3/00* (2006.01)
*A61B 3/12* (2006.01)

(56) References Cited

U.S. PATENT DOCUMENTS

| | | |
|---|---|---|
| 2007/0216909 A1 | 9/2007 | Everett et al. |
| 2007/0222945 A1* | 9/2007 | Tsukada ................. A61B 3/102 351/205 |
| 2008/0024721 A1 | 1/2008 | Ueno et al. |
| 2008/0100612 A1 | 5/2008 | Dastmalchi et al. |
| 2010/0149489 A1 | 6/2010 | Kikawa et al. |
| 2010/0278402 A1 | 11/2010 | Everett et al. |
| 2011/0043757 A1 | 2/2011 | Everett et al. |
| 2011/0058029 A1 | 3/2011 | Nakajima et al. |
| 2011/0301455 A1 | 12/2011 | Numajiri et al. |
| 2012/0075584 A1 | 3/2012 | Stetson |
| 2012/0127428 A1* | 5/2012 | Isogai .................... A61B 3/102 351/206 |
| 2012/0128222 A1 | 5/2012 | Everett et al. |
| 2012/0229765 A1 | 9/2012 | Makihira |
| 2012/0249956 A1 | 10/2012 | Narasimha-Iyer et al. |
| 2013/0181976 A1 | 7/2013 | Dastmalchi et al. |
| 2013/0222762 A1 | 8/2013 | Everett et al. |

FOREIGN PATENT DOCUMENTS

| | | |
|---|---|---|
| EP | 2497414 | 9/2012 |
| JP | 06-237900 | 8/1994 |
| JP | 09-094230 | 4/1997 |
| JP | 2008005987 A2 | 1/2008 |
| JP | 2008-029467 | 2/2008 |
| JP | 2009056246 A2 | 3/2009 |
| JP | 2010-012109 | 1/2010 |
| JP | 2011092702 A2 | 5/2011 |
| WO | 2006/105903 | 10/2006 |
| WO | 2010/101162 | 9/2010 |
| WO | 2012/130976 | 10/2012 |

OTHER PUBLICATIONS

Japanese Office Action mailed on Jan. 5, 2017 for the corresponding Japanese Patent Application No. 2012-241327 and its English translation.

Japanese Office Action mailed on Aug. 2, 2016 for the corresponding Japanese Patent Application No. 2012-241327 and its English translation thereof.

* cited by examiner

OPHTHALMOLOGIC PHOTOGRAPHING APPARATUS AND OPHTHALMOLOGIC PHOTOGRAPHING METHOD

CROSS-REFERENCE TO RELATED APPLICATION

This application claims priority from Japanese Patent Application No. 2012-241327 filed with the Japan Patent Office on Oct. 31, 2012, the entire content of which is hereby incorporated by reference.

BACKGROUND

1. Technical Field

The present disclosure relates to an ophthalmologic photographing apparatus and an ophthalmologic photographing method.

2. Related Art

An ophthalmologic photographing apparatus that captures a tomographic image of an examinee's eye is known. The ophthalmologic photographing apparatus scans the fundus with measurement light using an optical scanning unit (for example, a galvanometer mirror) to obtain a fundus image. Known examples of such an ophthalmologic photographing apparatus include an apparatus for capturing a fundus tomographic image, such as an optical coherence tomography (OCT) apparatus, and an apparatus for capturing a fundus front image, such as a scanning laser ophthalmoscope (Scanning Laser Ophthalmoscope; SLO) (see JP-A-2008-29467).

When an examiner observes a lesion area using such an ophthalmologic photographing apparatus, the examiner checks the lesion area (portion of interest) in a fundus front image and selects the position (portion) of the lesion area in the fundus front image. For example, when the examiner selects a desired scan line on the fundus front image, the apparatus displays one tomographic image corresponding to the selected scan position.

In the follow up, a tomographic image of the lesion area of the patient's eye is obtained under predetermined photographing conditions. Subsequently, tomographic images of the lesion, area are captured at intervals, and then compared with one another to observe the progress of the lesion.

SUMMARY

An ophthalmologic photographing apparatus includes: a photographing optical system including an optical scanner configured to scan an examinee's eye with measurement light and a detector configured to detect a coherent state of reflected light of the measurement light from the examinee's eye and reference light, the photographing optical system being configured to capture a tomographic image of the examinee's eye in response to an output signal from the detector; a reference data setting unit configured to set a photographing condition of a previously acquired captured image as reference data for a follow-up; an image capture data setting unit configured to set the reference data set by the reference data setting unit as image capture data for the follow-up; and a tomographic image acquisition controller configured to acquire a tomographic image of the examinee's eye by controlling the photographing optical system based on the reference data set as the image capture data.

DETAILED DESCRIPTION

Figure 1:
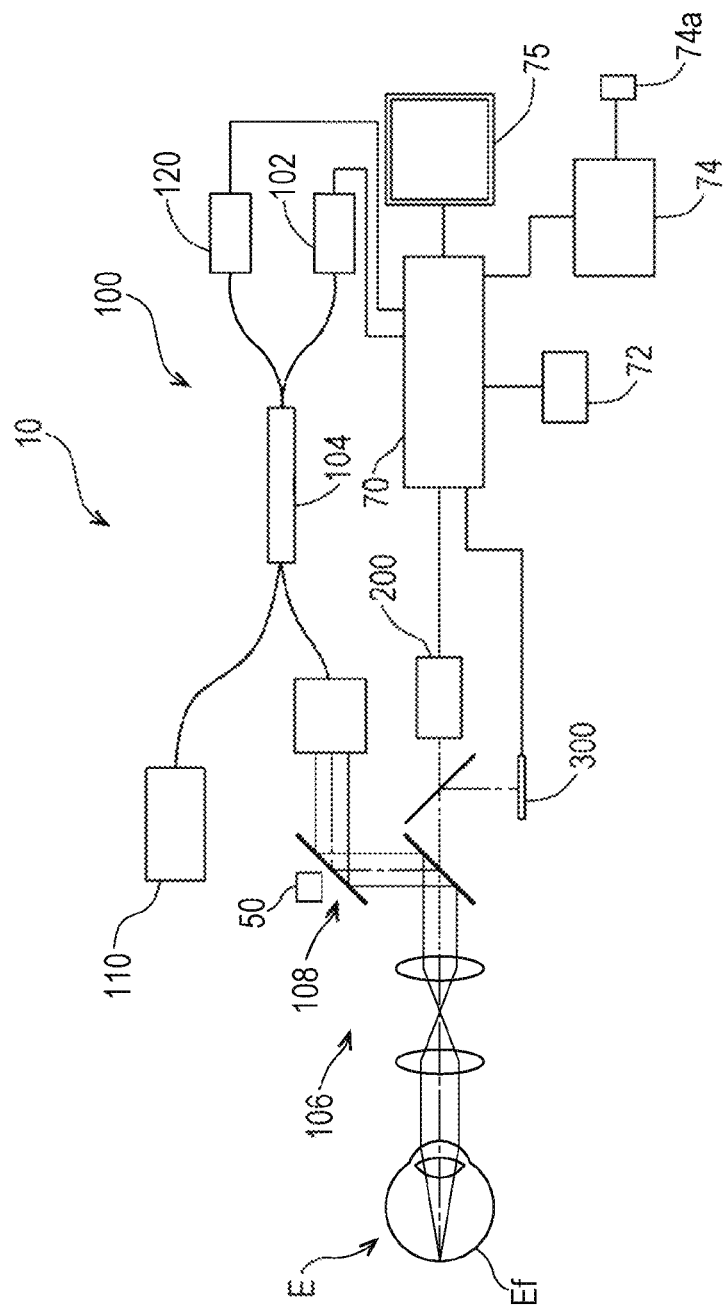
FIG. 1 is a diagram schematically illustrating the configuration of an ophthalmologic photographing apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Each patient has a different disease (lesion) and portion of the disease. Hence, a technique for capturing a lesion area in a fixed photographing pattern and observing its progress based on the image-capturing result has difficulty acquiring sufficient information to observe the progress of the lesion.

An object of the present disclosure is to provide an ophthalmologic photographing apparatus that can acquire sufficient information to observe the progression of a lesion in a patient by patient basis.

An ophthalmologic photographing apparatus according to an embodiment of the present disclosure includes the following configuration.

An ophthalmologic, photographing apparatus includes a photographing optical system including an optical scanner configured to scan an examinee's eye with measurement light and a detector configured to detect a coherent state of reflected light of the measurement light from the examinee's eye and reference light, the photographing optical system being configured to capture a tomographic image of the examinee's eye in response to an output signal from the detector, a reference data setting unit configured to set a photographing condition of a previously acquired captured image as reference data for a follow-up, an image capture data setting unit configured to set the reference data set by the reference data setting unit as image capture data for the follow-up, and a tomographic image acquisition controller configured to acquire a tomographic image of the examinee's eye by controlling the photographing optical system based on the reference data set as the image capture data.

The ophthalmologic photographing apparatus can acquire sufficient information to observe progression in a patient by patient basis.

The ophthalmologic photographing, apparatus according to the embodiment will be described with reference to FIGS. 1 to 6. FIG. 1 is a schematic block diagram illustrating the configuration of the ophthalmologic photographing apparatus according to the embodiment. In the embodiment, the axis direction of an examinee's eye (eye E) is set to be a Z direction, the horizontal direction to be an X direction, and the vertical direction to be a Y direction. Therefore, the surface direction of the fundus is the X-Y direction.

<Outline>

A description will be given of the outline of the ophthalmologic photographing apparatus according to the embodiment. An ophthalmologic photographing apparatus (optical coherence tomography device) 10 according to the embodiment includes a coherent, optical system (OCT optical system) 100, an observing optical system 200, a display unit (monitor) 75, an operation, unit 74, and a control unit (CPU) 70.

The coherent optical system (photographing optical system) 100 has a scanning unit (optical scanner) 108, and a detector 120, and obtains a tomographic image of the examinee's eye. The optical scanner 108 scans the examinee's eye two-dimensionally with light emitted from a light source 102. The detector 120 detects a coherent state of measurement light emitted from the light source, and reference light.

The operating unit 74 is operated by the examiner. The operating unit 74 may be, for example, a user interface such as a mouse 74a, a trackball, or a touchscreen.

The monitor 75 may be, for example, a display on a PC, or a display on the ophthalmologic photographing apparatus. The monitor 75 may be a touchscreen. If the monitor 75 is a touchscreen, the monitor 75 also functions as an operating unit.

As described above, the photographing optical system 100 includes the optical scanner 108 that scans the examinee's eye with the measurement light and the detector 120 that detects a coherent state of reflected light of the measurement light from the examinee's eye and the reference light, and captures a tomographic image of the examinee's eye in response to an output signal from the detector 120.

In the embodiment, the control unit 70 also serves as a reference data setting unit, an image capture data setting unit, a display controller, and a tomographic image acquisition controller. However, the control unit 70 is not limited to this, but may be provided as different members, or part of the members may also serve as another member.

Follow-up image capture of a captured image in the ophthalmologic photographing apparatus 10 will be described.

The examiner operates the operating unit 74 to select a captured image for setting reference data (a baseline) from at least one or more captured images previously acquired by the ophthalmologic photographing apparatus 10. If the examiner selects the captured image for setting reference data, the control unit 70 sets the selected captured image and a photographing condition of the captured image as reference data, for a follow-up.

Next, for example, the examiner operates the operating unit 74 to select reference data for follow-up image capture (image capture for the follow-up) from at least one or more reference data set from the captured image(s). The control unit 70 sets the selected reference data based on an operation signal from the operating unit 74 as image capture data for the follow-up from the at least one or more reference data.

For example, the setting of image capture data is not limited to the case where the setting is performed by the examiner selecting reference data. Upon initial setting of image capture data for follow-up image capture, reference data is set as described above and subsequently set as image capture data.

The photographing conditions may include at least any of a scan pattern, scan position information, optimization information, and fixation position information.

The control, unit 70 may set a captured image and accompanying information corresponding to the captured image, as well as the captured image, as reference data. The control unit 70 displays the reference data on the monitor 75. In this case, the control unit 70 displays the accompanying information, corresponding to the captured image, as well as the captured image, on a setting screen for setting the image capture data.

The accompanying information may be provided for enabling the recognition (identification) of the photographing condition of the captured image, the captured image, and the like. The control unit 70 may display the accompanying information with a name displayed on a tag 82 assigned to the reference data. The tag 82 may represent a name such as macular disease near the fovea, glaucoma around the optic disc, or glaucoma near the fovea (see FIG. 5). In this manner, a name is attached to each baseline. Consequently, the examiner can recognize, for example, the photographing condition(s) (for example, the photographing position, the scan pattern, and/or the fixation position) of each baseline and/or the purpose of image capture (for example, the observation of glaucoma). Consequently, the examiner can set image capture data by combining baselines (reference data) that the examiner desires. Furthermore, the examiner performs image capture based on the image capture data, which enables desired follow-up image capture.

The accompanying information may be set by the examiner operating the operating unit 74 to input characters, numerics, and/or the like. Moreover, the accompanying information may be set automatically based on the photographing condition. In this case, the control unit 70, for example, selects the name of the accompanying information from information such as the photographing position, the scan pattern, and the fixation position, and sets the accompanying information.

The captured images previously acquired by the ophthalmologic photographing apparatus 10 may be captured images successively captured by the ophthalmologic photographing apparatus 10 under a plurality of different photographing conditions. In such a case, the control unit 70 sets as the reference data the captured image selected by the operation of the operating unit 74, and the photographing condition of the captured image in a collective manner. Such successive image captures include, for example, combo photographing that successively performs plurality of image captures on a preset given photographing condition. For example, if image captures are successively and sequentially performed in a plurality of scan patterns as the combo photographing, the plurality of scan patterns in die combo photographing is set as baselines in a collective manner. In this manner, baselines in a plurality of image captures can be set in a collective manner, which makes the settings of baselines and image capture data efficient and easy.

At the time of follow-up image capture, the control unit 70 controls the optical scanner 108 based on the photographing condition of the reference data set as the image capture data to acquire a tomographic image of the examinee's eye.

The control unit 70 sets the image capture data, for example, by combining a plurality of reference data. In this case, the control unit 70 controls the optical scanner 108 (the photographing optical system 100) based on the photographing condition of each of the plurality of reference data set as the image capture data. Consequently, the control unit 70 successively acquires tomographic images of the fundus of the examinee's eye under respective photographing conditions of the plurality of reference data. Consequently, the follow-up image captures for the baselines are successively performed. Hence, the follow-up image capture can be performed smoothly while time and trouble are reduced.

Even after the image capture data is set, the combination of baselines can be edited. For example, the examiner selects the reference data added or deleted at the time of the follow-up image capture. If the examiner selects at least either to add the reference data to the image capture data or delete the reference data from the image capture data after the setting of the image capture data, the control unit 70 resets image capture data. In this manner, a baseline in image capture data can be changed. Hence, a follow-up under different photographing conditions becomes possible. Consequently, it becomes possible to deal with, for example, a case where a follow-up is desired on a photographing condition of other than the set baseline due to the large progression of a lesion area. Moreover, the baseline in the image capture data can be deleted. Hence, there will be no need of excess image capture. Consequently, follow-up image capture can be performed smoothly.

The configuration or operation of the embodiment is not limited to the above-mentioned aspect. For example, ophthalmologic photographing software (program) that executes the functions of the embodiment may be provided to an ophthalmologic photographing system or an ophthalmologic photographing apparatus via a network or various recording media (for example, a memory 72 (described below)). A computer (for example, a CPU) of the ophthalmologic photographing system or the ophthalmologic photographing apparatus can also read and execute the program.

The ophthalmologic photographing apparatus 10 may include both the optical scanner 108 and the detector 120. The optical scanner 108 scans the examinee's eye with light emitted from the light source. The detector 120 detects a coherent state of the reflected light of the measurement light irons the examinee's eye, the measurement light having been emitted from the light source, and the reference light. The ophthalmologic photographing program is executed by the control apparatus (the control unit 70) of the ophthalmologic photographing apparatus 10. The control apparatus controls the operation of the ophthalmologic photographing apparatus 10 that captures a tomographic image (tomographic image) of an examinee's eye in response to an output signal from the detector 120. The ophthalmologic photographing program is executed by a processor of the control apparatus. In other words, the control apparatus (processor) that has read the ophthalmologic photographing program executes a reference data setting step, an image capture data setting step, and a control step. In the reference data setting step, a photographing condition of a captured image selected by the operation of the operating unit 74 from captured images previously acquired by the ophthalmologic photographing apparatus 10 that captures a tomographic image of art examinee's eye is set as reference data for a follow-up. In the image capture data setting step, reference data selected by the operation of the operating unit 74 from at least one or more reference data set in the reference data setting step is set as image capture data for the follow-up. In the control step, the ophthalmologic photographing apparatus 10 is controlled based on the photographing condition of the reference data, which was set as the image capture data in the image capture data, setting step to acquire a tomographic image.

Embodiment

FIG. 1 is a diagram schematically illustrating the configuration of an ophthalmologic photographing apparatus according to an embodiment. The apparatus is the ophthalmologic photographing apparatus (optical, coherent tomography device) 10 configured to capture a tomographic image of a fundus Ef of an examinee's eye E. The ophthalmologic photographing apparatus 10 includes the coherent optical system (OCT optical system) 100, the frontal-view observing optical system 200, a fixation target projecting unit 300, and the calculation control part (CPU) 70.

The OCT optical system 100 irradiates the fundus with measurement light. The OCT optical system 100 detects the coherent state of the measurement light reflected by the fundus and reference light by the light-receiving device (the detector 120). The OCT optical system 100 includes an irradiation position-changing unit (e.g., the optical scanner 108 and the fixation target projecting unit 300) that changes the irradiation position of the measurement light on the fundus Ef in order to change a capturing position on the fundus Ef. The control unit 70 controls the operation of the irradiation position-changing unit based on the set capturing position information. The control unit 70 acquires a tomographic image in response to a light-receiving signal from the detector 120.

<OCT Optical System>

The OCT optical system 100 is configured as a so-called an ophthalmic optical coherence tomography (OCT) apparatus, and captures a tomographic image of the eye E. The OCT optical system 100 allows a coupler (light splitter) 104 to split light emitted from the measurement light source 102 into measurement light (sample light) and reference light. The OCT optical system 100 allows a measuring optical system 106 to lead the measurement light to the fundus Ef of the eye E. Moreover; the OCT optical system 100 leads the reference light to a reference optical system 110. Coherent light obtained fey combining the measurement light reflected by the fundus Ef and the reference light is subsequently received by the detector (light-receiving device) 120.

The detector 120 detects the coherent state of the measurement light and the reference light. In Fourier domain OCT, the spectral intensity of the coherent light is detected by the detector 120. The spectral intensity data is Fourier transformed to acquire a depth profile (A-scan signal) in a predetermined range. Fourier domain OCT includes, for example, Spectral-domain OCT (SD-OCT), Swept-source OCT (SS-OCT), and Time-domain OCT (TD-OCT).

The optical scanner 108 scans the fundus of the examinee's eye with light from the measurement light source. For example, the optical scanner 108 scans the fundus two-dimensionally (in the X-Y direction (transverse direction)) with the measurement light. The optical scanner 108 is disposed at a position that is substantially conjugated with the pupil. The optical scanner 108 has two galvanometer mirrors, for example. The reflection angles of these galvanometer mirrors are arbitrarily adjusted by a drive mechanism 50.

Consequently, it becomes possible to change a reflection (travel) direction of light flux emitted from the light source 102. Therefore, it is possible to scan the fundus in an arbitrary direction with the measurement light. Consequently, it becomes possible to change the capturing position on the fundus Ef. It is sufficient if the optical scanner 108 is configured to deflect light. A reflective mirror (a galvanometer mirror, polygon mirror, or resonant scanner), an acousto-optic modulator (AOM) that changes the travel (deflection) direction of light, or the like is used as the optical scanner 108.

The reference optical system 110 generates reference light to be combined with reflected light acquired by the reflection of the measurement light from the fundus Ef. The reference optical system 110 may be the Michelson system or Mach-Zehnder system. The reference optical system 110 includes, for example, a catoptric system (e.g., a reference mirror).

The reference optical system 110 causes the catoptric system to reflect light from the coupler 104 to return the light to the coupler 104 again and leads it to the detector 120. In another example, the reference optical system 110 includes a transmission optical system (e.g., an optical fiber). The reference optical system 110 does not return the light from the coupler 104 but allows the light to pass therethrough to lead the light to the detector 120.

The reference optical system 110 includes a member for changing a difference in optical path length between measurement light and reference light by moving an optical member on a reference optical path. In the reference optical system 110, the reference mirror is moved in the optical axis direction, for example. A member to change the difference in optical path length (to adjust the optical path length) may be disposed on a measurement optical path of the measuring optical system 106.

<Frontal-View Observing Optical System>

The frontal-view observing optical system (front image observing device) 200 is provided to obtain a front image (frontal image) of the fundus Ef. The observing optical system 200 has a device configuration of what is called an ophthalmic scanning laser ophthalmoscope (SLO), for example. The observing optical system 200 includes, for example, an optical scanner and a light-receiving device. The optical scanner scans the fundus two-dimensionally with measurement light (e.g., infrared light) emitted from a light source. The light-receiving device receives fundus reflected light via a confocal opening disposed at a position that is substantially conjugated with the fundus.

The observing optical system 200 may have the configuration of what is called a fundus camera type. Moreover, the OCT optical system 100 may also serve as the observing optical system 200. In other words, a front image may be acquired using data forming a tomographic image, the data being obtained two-dimensionally. The data include, for example, an integral image in a depth direction of a three-dimensional tomographic image, an integrated value of spectral data at the positions of X and Y, or luminance data at the positions of X and Y in a certain depth direction, and a retinal surface layer image.

<Fixation Target Projecting Unit>

The fixation target projecting unit 300 includes an optical system for guiding a direction of the visual line of the eye E. The projecting unit 300 includes a fixation target to be presented to (projected on) the eye E, and can guide the visual line of the eye E to a plurality of directions.

For example, the fixation target projecting unit 300 includes a visible light source that emits visible light, and changes a position to present the target two-dimensionally. If the direction of the visual line is changed, therefore, it leads to a change in capturing position. For example, if the fixation target is presented from the same direction as the photographing optical axis, the center portion of the fundus is set as a photographed portion. Moreover, if the fixation target is presented above the photographing optical axis, the upper part of the fundus Is set as a photographed portion. In other words, a photographing portion is changed in accordance with the position of the target, relative to the photographing optical axis.

Cited as the fixation target projecting unit 300 are, for example, a configuration to adjust a fixation position by adjusting the lighting state of a plurality of LEDs arranged in a matrix fashion, and a configuration to adjust a fixation position by combining a scan by an optical scanner using the light of a light source and control over the lighting up and out of the light source. Moreover, the projecting unit 300 may be an internal or external fixation light type.

<Controller>

The control unit 70 controls the entire apparatus including the members 100 to 300. Moreover, the control unit 70 also serves as an image processor that processes an image acquired, an image analyzer that analyzes art image acquired, and the like. The control unit 70 is implemented by a general CPU (Central Processing Unit), and the like. The control unit 70 analyzes the fundus Ef based on a tomographic image as indicated below.

The control unit 70 acquires a tomographic image by performing image processing on a light-receiving signal output from the detector 120 of the OCT optical system 100. Furthermore, the control unit 70 acquires a front image in response to a light-receiving signal output from the light-receiving device of the frontal-view observing optical system 200. Moreover, the control unit 70 controls the fixation target projecting unit 300 to change a fixation position.

The memory (storage unit) 72, the monitor 75, and the control unit (operating unit) 74 are electrically connected to the control unit 70, respectively. The control unit 70 controls a display screen of the monitor 75. An acquired fundus image is output to the monitor 75 as a still image or moving image as well as is stored in the memory 72. For example, a photographed tomographic image (e.g., a three-dimensional tomographic image), a front image, and various kinds of information on photographing such as the capturing position information of the tomographic image are recorded in the memory 72. The memory 72 stores a control program (ophthalmologic photographing program) for controlling the operation of the present apparatus (ophthalmologic photographing apparatus 10).

The various pieces of information on a captured image are stored and managed in the memory 72 on a patient by patient basis. For example, the various pieces of information of each patient are identified with an ID assigned to an individual patient. The examiner inputs the ID of a patient on an image capture screen, an analysis screen, or the like. Thus, the captured image can be stored in the memory 72 as information of the patient having the input ID. Moreover, the ID is input to read various pieces of information of the patient corresponding to the ID from the memory 72 and display the information on the monitor 75. A patient ID is newly registered, for example, when the apparatus is switched on, and is then assigned to each patient. For example, if image capture is performed for a new patient, the examiner inputs a new patient ID to create data for the new patient. In this case, for example, information on gender, name, birth date, and the like, as well as the patient ID, is input. These pieces of information are registered in the memory 72.

The control unit 70 controls the OCT optical system 100, the frontal-view observing optical system 200, and the fixation target projecting unit 300, in response to an operation signal output from the operating unit 74. The operating unit 74 is connected to the mouse 74a as operating members to be operated by the examiner.

The monitor 75 may be a display monitor mounted on the apparatus main body or a display monitor of a personal computer. Alternatively, the monitor 75 may include a combination of these display monitors.

In the embodiment, a description will be given taking a case where the OCT optical system 100 also serves as the observing optical system 200 as an example. The control unit 70 controls the optical scanner 108 to scan the examinee's eye with the measurement light two-dimensionally. The control unit 70 obtains a tomographic image and a front image as moving images based on a light receiving signal output from the detector 120. The control unit 70 then displays the obtained tomographic image and front image on the monitor 75.

A description will be given of the control operation of the ophthalmologic photographing apparatus 10 including the above configuration. The control unit 70 executes processes described below pursuant to the control program stored in the memory 72. The examiner instructs the examinee to fix his/her eye on the fixation target of the fixation target projecting unit 300. The examinee's eye is subsequently captured by an unillustrated anterior segment observing camera. In this case, the examiner uses an unillustrated joystick and adjusts alignment so as to locate the measurement light axis at the pupil center of the examinee's eye while watching the anterior segment observation image on the monitor 75.

The control unit 70 then controls the optical scanner 108 to scan the fundus with measurement light in a predetermined direction. The control unit 70 acquires a light-receiving signal corresponding to a predetermined scan area from an output signal output from the detector 120 during the scan. The control unit 70 forms a fundus image in response to the light-receiving signal.

Hereinafter, an example of a method for acquiring a fundus tomographic image (hereinafter described as the tomographic image) and a fundus front image (hereinafter described as the front image) according to the embodiment will be illustrated. The control unit 70 performs image processing an spectral data detected by the detector 120 to form the tomographic image sod the front image. The tomographic image and the from image may be simultaneously, alternatively, or sequentially acquired. In other words, the spectral data is used to acquire at least either the tomographic image or the front image. The acquired tomographic image and front image are displayed on the monitor 75.

The examiner operates an unillustrated photographing switch at a desired position. The control unit 70 starts acquiring a three-dimensional tomographic image of the front and tomographic images displayed on the monitor 75 in response to the operation of the photographing switch. The acquired three-dimensional tomographic image is stored as a still image in the memory 72.

The control unit 70 controls the OCT optical system 100 to acquire a three-dimensional tomographic image corresponding to a set region. The control unit 70 then acquires a three-dimensional tomographic image by the OCT optical system 100 at any time. A three-dimensional tomographic image includes image data where A-scan signals are arranged two-dimensionally with respect, to the X and Y directions, and a three-dimensional graphic image.

When obtaining a three-dimensional tomographic image, the control unit 70 controls the optical scanner 108 to scan a scan area corresponding to an image capture area two-dimensionally with the measurement light in the X and Y directions. With such a scan, a three-dimensional tomographic image is acquired. Scan patterns for obtaining a three-dimensional tomographic image include, for example, a raster scan and a radial scan.

<Follow-Up Image Capture>

The ophthalmologic photographing apparatus 10 according to the embodiment has a follow-up image capture function. Hereinafter, the follow-up image capture will be described.

The examiner switches on the ophthalmologic photographing apparatus 10 and subsequently operates the operating unit 74 to input a predetermined patient ID. If the patient ID is input, the control unit 70 displays a reference screen for a patient, corresponding to the input ID. The reference screen includes an initial screen. A captured image of the patient, various pieces of information such as age and gender, various selection switches to shift to image capture or image analysis, and the like are listed and displayed on the initial screen (the details are described below).

The examiner operates the operating unit 74 to select on the reference screen the photographing switch to shift to image capture. If the photographing switch, is selected, the control unit 70 switches the display screen of the monitor 75 from the reference screen to the image capture screen to capture a tomographic image. Consequently, image capture can be performed for the patient corresponding to the Input ID.

<Setting of Photographing Conditions>

Figure 2:
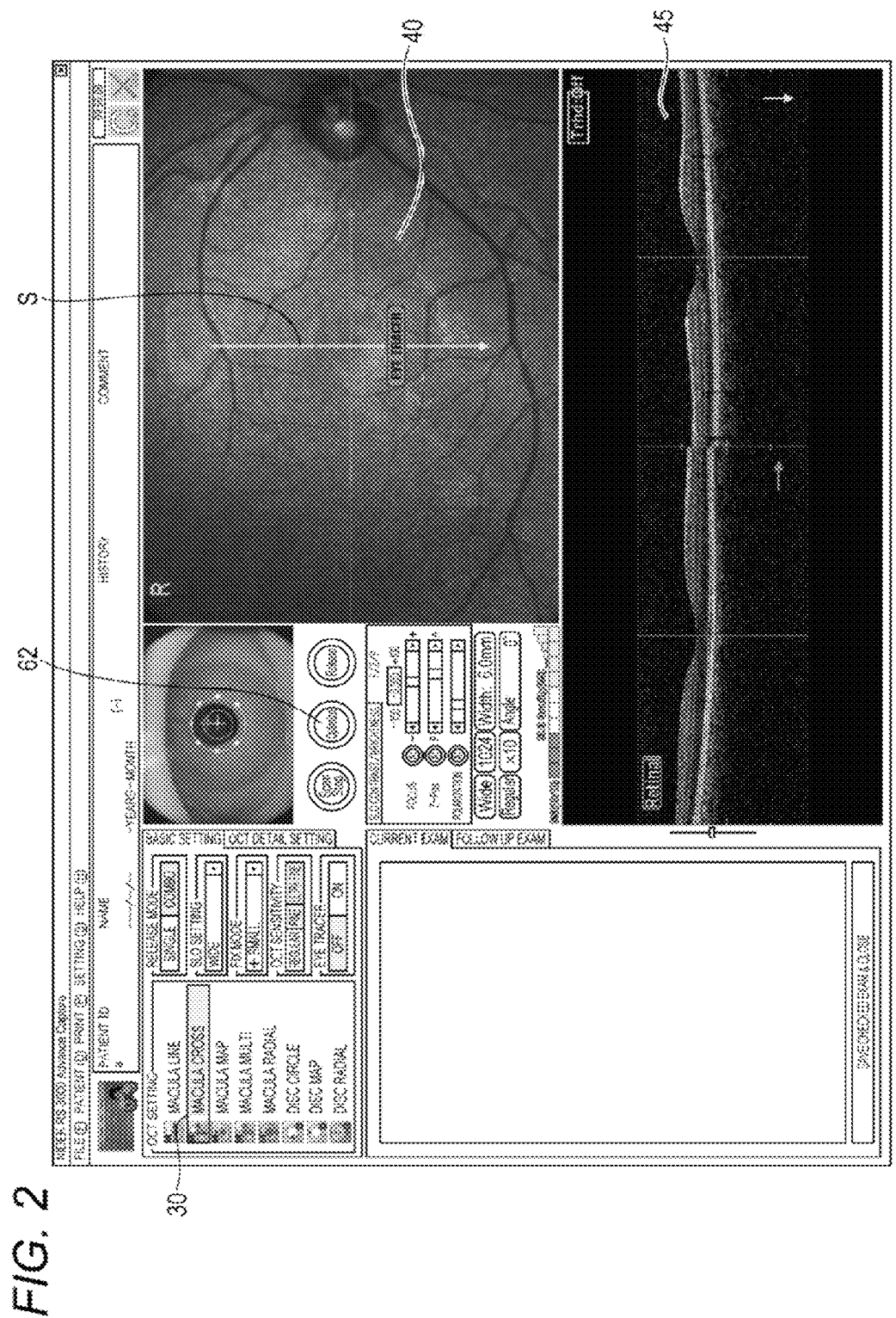
FIG. 2 is a diagram illustrating an exemplary image capture screen of a tomographic image and a front image.
Figure 3:
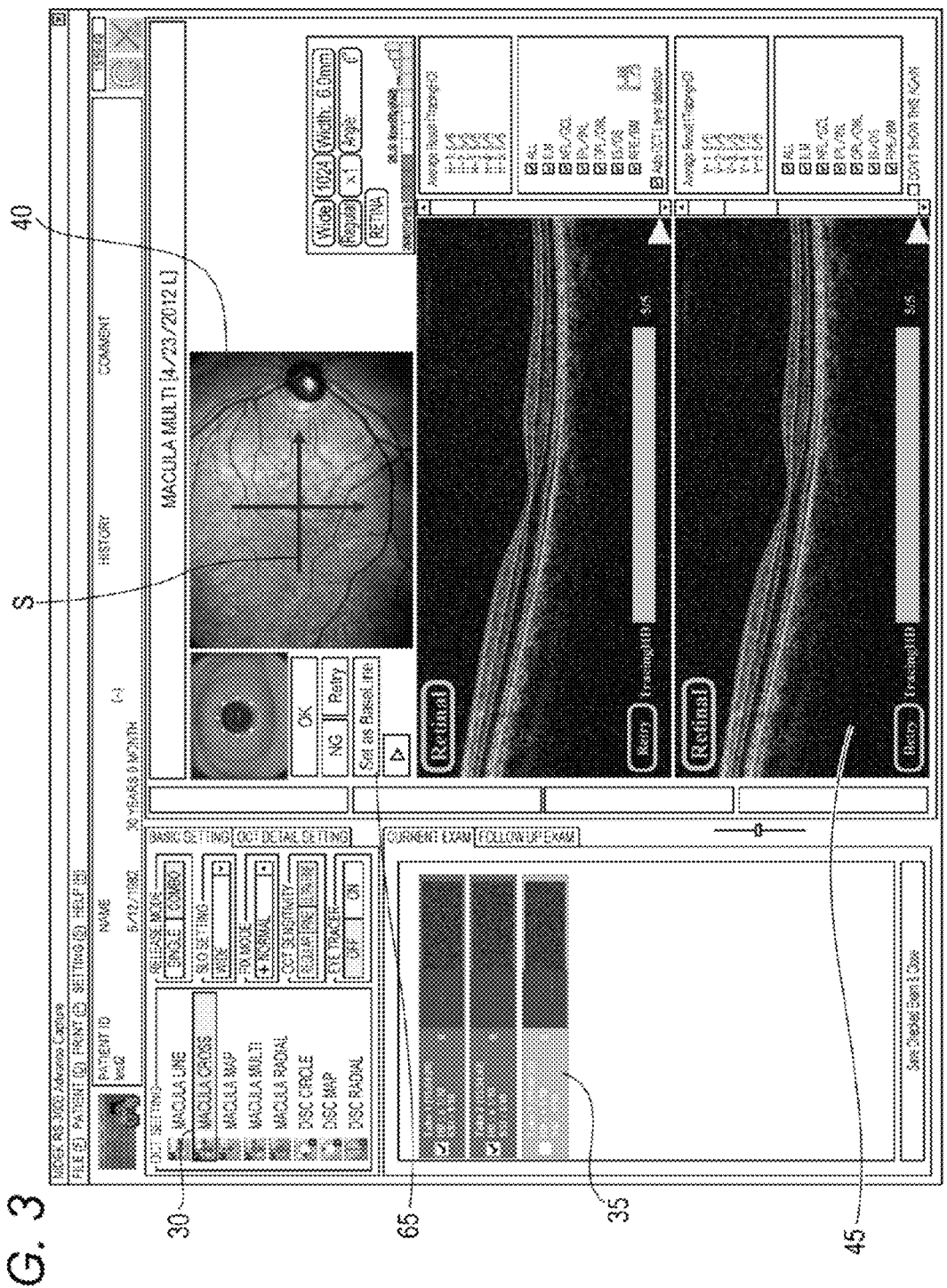
FIG. 3 is a diagram illustrating an exemplary confirmation screen immediately after image capture of a tomographic image and a front image.

FIG. 2 is a diagram illustrating an exemplary image capture screen of the tomographic image and the front image. Moreover, FIG. 3 is a diagram illustrating an exemplary confirmation screen immediately after capturing the tomographic Image and the front image. Image capture is performed in accordance with the operation of the examiner to acquire the front image and the tomographic image. Consequently, the display screen of the monitor 75 is switched from the image capture screen (See FIG. 2) to the confirmation screen (see FIG. 3). The save of a captured image, the setting of a baseline, and the like are performed on the confirmation screen, (the details are described below).

A front image 40, a tomographic image 45, and a scan line S are displayed on the image capture screen (see FIG. 2). The scan line S is displayed on the front image 40. The scan line S is a target that electronically displays an acquisition position of the tomographic image 45 on the front image 40.

At the time of image capture, the examiner operates the operating unit 74 to set the photographing conditions. The photographing conditions include, for example, the scan pattern, the scan position (tomographic image acquisition position), optimization control, and the fixation position. The optimization control, includes, for example, the adjustment of an optical path length, the focus adjustment, the adjustment of the polarization state. The photographing conditions may include the image capture elate or left/right eye information (information indicating which of the left or right eye).

For example, if the scan position is set, the examiner operates the operating unit 74 to move the display position of the scan line S on the front image 40. The control unit 70 moves the display position of the scan line S on the front image 40 based on an operation signal input from the operating unit 74. The scan position of the measurement light by the optical scanner 108 is set at a position (portion) corresponding to the scan line S on the front image 40.

The method for setting the scan position is not limited to this. For example, a pointer that can move over the front image may be displayed, on the monitor 75. The pointer may be, for example, a cross mark, a dot mark, a pen mark, or an arrow. The examiner may move the pointer to move the target (scan position) over the front image and set the scan position of the measurement light.

Moreover, for example, if the scan pattern is set, the examiner operates the operating unit 74 to select the scan pattern from a scan pattern list 30. The scan pattern may be, for example, a line scan, a cross scan, a map scan, a multi-scan, a radial scan, or a circle scan. The control unit 70 changes the display of the shape of the scan line S on the front image 40 to the display of the set scan pattern based on an operation signal input from the operating unit 74.

If the optimization control is performed, the examiner, for example, operates the operating unit 74 to select an optimization start switch 62. The control unit 70 emits a trigger signal for starting the optimization control to start the optimization control operation. The control unit 70 performs the optical path length adjustment, the focus adjustment, and the polarization state adjustment (polarizer adjustment). For example, an unillustrated focusing optical member (focusing lens) that can move in the optical axis direction is used for the focus adjustment. In the focus adjustment, the focusing lens is moved in the optical axis direction to correct the diopter scale to the fundus of the examinee's eye. In the polarizer adjustment, the control unit 70 drives an unillustrated polarizer (polarizing element) arranged on the optical path of the measurement light or the optical path of the reference light such that the polarizing states of the measurement light and the reference light are brought into substantially agreement.

If the examiner sets the photographing conditions and operates the unillustrated photographing switch, the control unit 70 acquires (captures) the front and tomographic images displayed on the monitor 75. When image capture is completed, the screen is shifted to the confirmation screen for the image captured. The captured front image 40 and tomographic image 45 are displayed on the confirmation screen (see FIG. 3). The scan line S indicating the photographing position is displayed on the front image. Moreover, a list 35 where captured images are listed and displayed is displayed on the confirmation screen. The examiner operates the operating unit 74 to make it possible to select a captured image from the list 35 and to select whether or not a captured image is stored in the memory 72.

<Reference Data (Baseline) Setting>

A description will be given of a method for observing progress using a captured image. Firstly, the examiner selects a specific captured image from captured images (front and tomographic images) captured on a predetermined photographing condition. The specific captured image becomes reference data (a baseline) for a follow-up.

The examiner selects a baseline setting switch 65 displayed on the monitor 75 of the image capture screen, on the confirmation screen after image capture (see FIG. 3). The control unit 70 then displays on the monitor 75 an input screen 66 for setting as a baseline a captured image and its photographing condition, which are displayed on the monitor 75.

Figure 4:
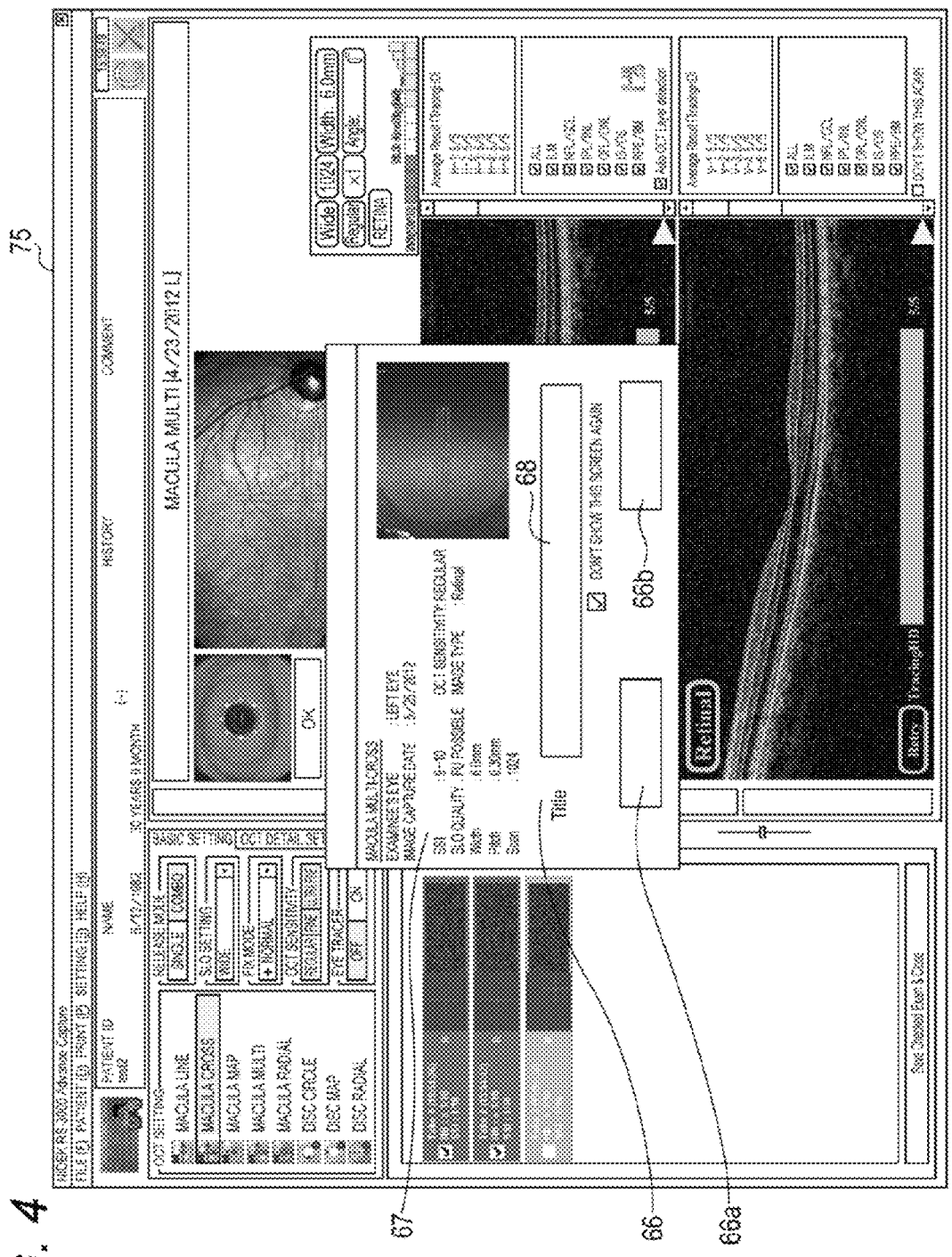
FIG. 4 is a diagram illustrating an exemplary input screen for setting a baseline displayed on a monitor.

FIG. 4 is an exemplary diagram illustrating the input screen 66 for setting a baseline, the input screen 66 being displayed on the monitor 75. When a baseline is set, the control unit 70 displays on the monitor 75 the input screen 66 for entering the name (title) of a tag assigned to the baseline.

For example, a front image 67, a title input field 68, a decision button 66a, a cancel button 66b, and the like are displayed on the input screen 66. A front image set as the baseline is displayed as the front image 67. An input field for inputting the name of a tag is illustrated as the title input field 68. The decision button 66a is used to set a captured image and its photographing conditions as a baseline and store them in the memory 72. The cancel button 66b is used to cancel the setting of a captured image and its photographing conditions as a baseline. If the cancel button 66b is selected, the screen returns to the image capture screen. An arbitrary tomographic image, in addition to the front image 67, may be displayed on the input screen.

For example, the examiner operates the operating unit 74 to input characters, numerics, and the like that express a title in the title input field 68 on the input screen. The examiner selects the decision button 66a after inputting the title, the control unit 70 stores the captured image and its photographing conditions as a baseline in the memory 72.

A baseline is set and managed on a patient by patient basis. In other words, a baseline is stored in the memory 72 on a patient ID by patient ID basis. Moreover, a baseline has a tag assigned to each baseline. The characters, numerics, and the like that the examiner has input in the title input field 68 are stored as the name (title) of the tag. The tag is used, for example, to identify a baseline when a plurality of baselines is set. In other words, tags having respective different names are displayed, each associated with a baseline. The name of a tag is checked, and each baseline can be then identified (the details are described below). The title of the tag can be edited also after the setting of the baseline.

In the embodiment, the name of a tag is set on the input screen 66 for setting the baseline. The embodiment is not limited to this, but the title of a tag can be set at any time. For example, the title may be set on the analysis screen upon the observation of a captured image. A tag may not be assigned to a baseline. Alternatively, the content set for the photographing condition (for example, the name of a scan pattern) may be displayed on a tag instead of the title.

Moreover, the name of a tag may be assigned automatically. For example, the control unit 70 may select the name of a tag based on information such as the photographing position, and the scan pattern and fixation position at the time of image capture.

As described above, a baseline to be used for a follow-up is set based on a captured image. In the embodiment, the description has been given taking as an example the case of selecting at the time of image capture whether or not to set a captured image as a baseline. The embodiment is not limited to this, but it is sufficient if a captured image is a previously captured image. For example, a captured image set as a baseline may be selected from the list 35. Moreover, for example, the examiner may set a baseline using the analysis screen or the reference screen (reference image) for observing a captured image. The analysis screen, is a display screen for analysis. In other words, the analysis screen is used to detect the layer from a captured tomographic image and create and display a layer thickness map and the like (the details are displayed, below).

<Setting of Image Capture Data>

The examiner can check the baseline set as described above on the reference screen. Hereinafter, a description will be given of the operation of follow-up image capture after the setting of the baseline.

Figure 5:
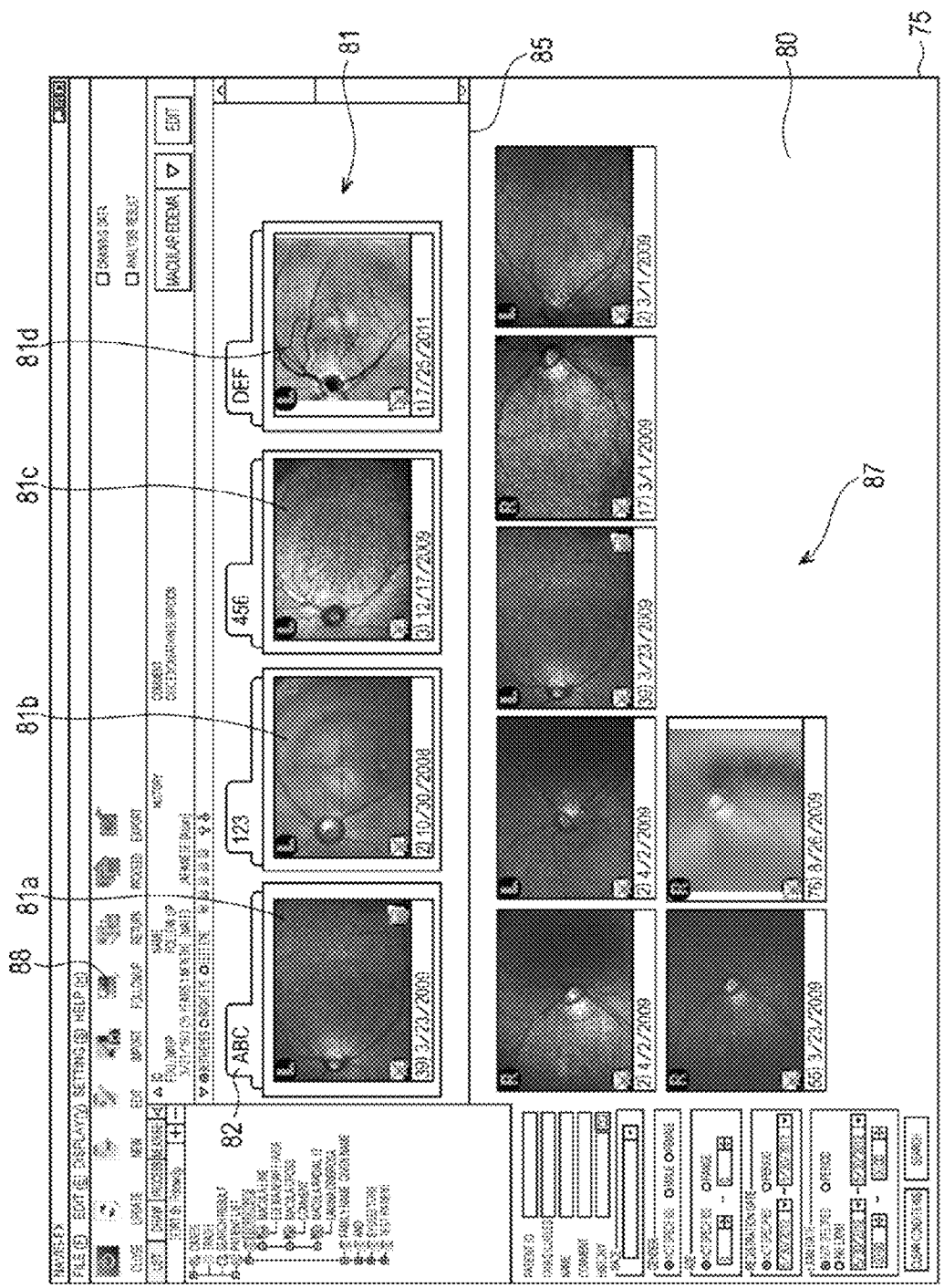
FIG. 5 is a diagram illustrating an exemplary reference screen.

FIG. 5 is an exemplary diagram illustrating the reference screen. The image capture result of the patient, various pieces of information (for example, age and gender) of the patient, and the like are listed and displayed on a reference screen 80. The reference screen 80 is managed by being stored in the memory 72 on a patient by patient basis. The reference screen 80 is identified with an ID assigned to an individual patient. For example, as described above, a switching signal to the reference screen is output after the completion of image capture, and the image capture screen is then switched to the reference screen 80. The switching signal is output, for example, when a photographing completion switch is selected, when a captured image is decided whether or not to be saved in the memory 72, or when the selection switch to the reference screen is selected. Moreover, if image capture is performed over different dates, upon the shift from the image capture screen to the reference screen 80, the examiner inputs a patient ID, and then the control unit 70 reads the reference screen 80 of a patient having the input ID from the memory 72 and displays the reference screen 80 on the monitor 75.

For example, a baseline group 81, a boundary line 85, a captured image group 87, and the like are displayed on the reference screen 80. The baseline group 81 includes a plurality of captured images set as baselines, which are lined and displayed. In other words, the baseline group 81 includes a plurality of baselines 81a to 81d lined and displayed. The captured image group 87 includes lined and displayed captured images that are not set as the baselines. The boundary line 85 indicates the boundary between the baseline group 81 and the captured image group 87. The baseline group 81 is displayed above the boundary line 85. The captured image group 87 is displayed below the boundary line 85.

The examiner selects at least one or more baselines used for follow-up image capture from the baseline group 81. In other words, the examiner can combine baselines selected from the baseline group when performing the follow-up image capture.

The examiner checks the name of the tag 82 attached to each baseline and accordingly can recognize the photographing conditions and/or purpose of photographing of a baseline. In other words, the examiner recognizes by the tag 82 the photographing conditions stored on a baseline by baseline basis and accordingly sets image capture data used for the follow-up image capture.

A name such as macular disease near the fovea, glaucoma around the optic disc, or glaucoma near the fovea is attached to the tag 82. In this manner, a name is attached to each baseline, and then die examiner can recognize die photographing conditions (for example, the photographing position, the scan pattern, and the fixation position) under which an individual baseline was captured. Alternatively, a name is attached to each baseline, and then the examiner can recognize the purpose of photographing of a baseline (for example, the observation of glaucoma), and the like. In this manner, the examiner combines baselines that the examiner desires to set image capture data. Image capture is performed based on the image capture data, and then desired follow-up image capture becomes possible to be performed. The examiner can also recognize the photographing conditions from not the information on the tag 82 but an image. For example, the examiner checks the scan line S displayed on the acquired front image 40, and the like, and therefore can check the photographing conditions.

The tag 82 may not be a tag in display form illustrated in FIG. 5. It is sufficient if the tag 82 has an aspect that can recognize the photographing condition and/or the purse of photographing of a baseline. The tag 82 can be displayed in various forms. For example, the tag 82 may be arranged in the vicinity of an image of a baseline, or superimposed and displayed on a captured image. Alternatively, only titles of the tags 82 may be listed and displayed.

For example, if performing follow-up image capture to observe glaucoma, the examiner looks at the tag 82 and selects a baseline for the follow-up image capture of glaucoma from the baseline group 81. If the examiner operates the operating unit 74 to select a baseline, the selected baseline is surrounded by a frame. For example, the frame is colored or the like. The addition of the frame is a discrimination method for discriminating between the selected baseline and an unselected baseline. The discrimination method is not limited to the addition of a frame, but, for example, may be a change in the tag of the selected baseline or the color of the whole baseline.

If the examiner selects a baseline, the control unit 70 sets the selected baseline as image capture data. The image capture data is set for each of the examinee's left and right eyes. In the embodiment, the setting of image capture data and image capture are performed, eye by eye, for the examinee's left and right eyes. After the setting of image capture data and image capture are completed for one of the eyes, the setting of image capture data and image capture are performed for the other eye.

In the embodiment, after the setting of image capture data and image capture are completed for one of the eyes, the setting of image capture data and image capture are performed for the other eye. The embodiment is not limited to this, but, for example, the settings of image capture data are performed for the left and right eyes in a collective manner and then image captures are performed sequentially for the left and right eyes. In this case, after image capture of one of the eyes is completed, the other eye is successively captured. If the left and right eyes are successively captured, when image capture of one of the eyes is completed, the apparatus main body may be moved automatically to the other eye to start image capture. Moreover, the examiner operates the unillustrated joystick or the like to move the apparatus main body to the other eye and perform image capture. In this case, while the apparatus main body is moved to the other eye, the image capture screen may be switched automatically by the moving amount to the one for image capture of the other eye. Alternatively, the image capture screen may be switched by the selection switch or the like.

After the setting of the image capture data, follow-up image capture is performed based on the photographing conditions of the baseline selected as the image capture data.

In the embodiment, the image capture data can be changed also after the setting of the image capture data. In other words, the image capture data can be changed as appropriate. For example, even if the image capture data was already set, a new baseline can also be selected as the image capture data from baselines that had not been set as the image capture data by the examiner operating the operating unit 74. The control unit 70 adds the new baseline to the existing image capture data to reset the image capture data. Moreover, even if the image capture data, was already set, the set baseline can also be selected to be deleted from the image capture data by the examiner operating the operating unit 74. The control unit 70 deletes the selected baseline from the existing image capture data to reset the image capture data.

In this manner, the baseline in the image capture data can be changed. Hence, a follow-up under different photographing conditions becomes possible. Consequently, it becomes possible to deal with, for example, a case where a follow-up is desired on a photographing condition other than the set baseline due to the large progression of a lesion. Moreover, the baseline in the image capture data can be deleted. Hence, there will be no need of excess image capture. Consequently, follow-up image capture can be performed smoothly.

<Image Capture Operations>

If the image capture data is set, the examiner operates the operating unit 74 to select the photographing switch for shifting to the image capture of an image on the reference screen 80. If the photographing switch is selected, the control unit 70 switches the display screen of the monitor 75 from the reference screen 80 to the image capture screen for capturing a tomographic image.

Figure 6:
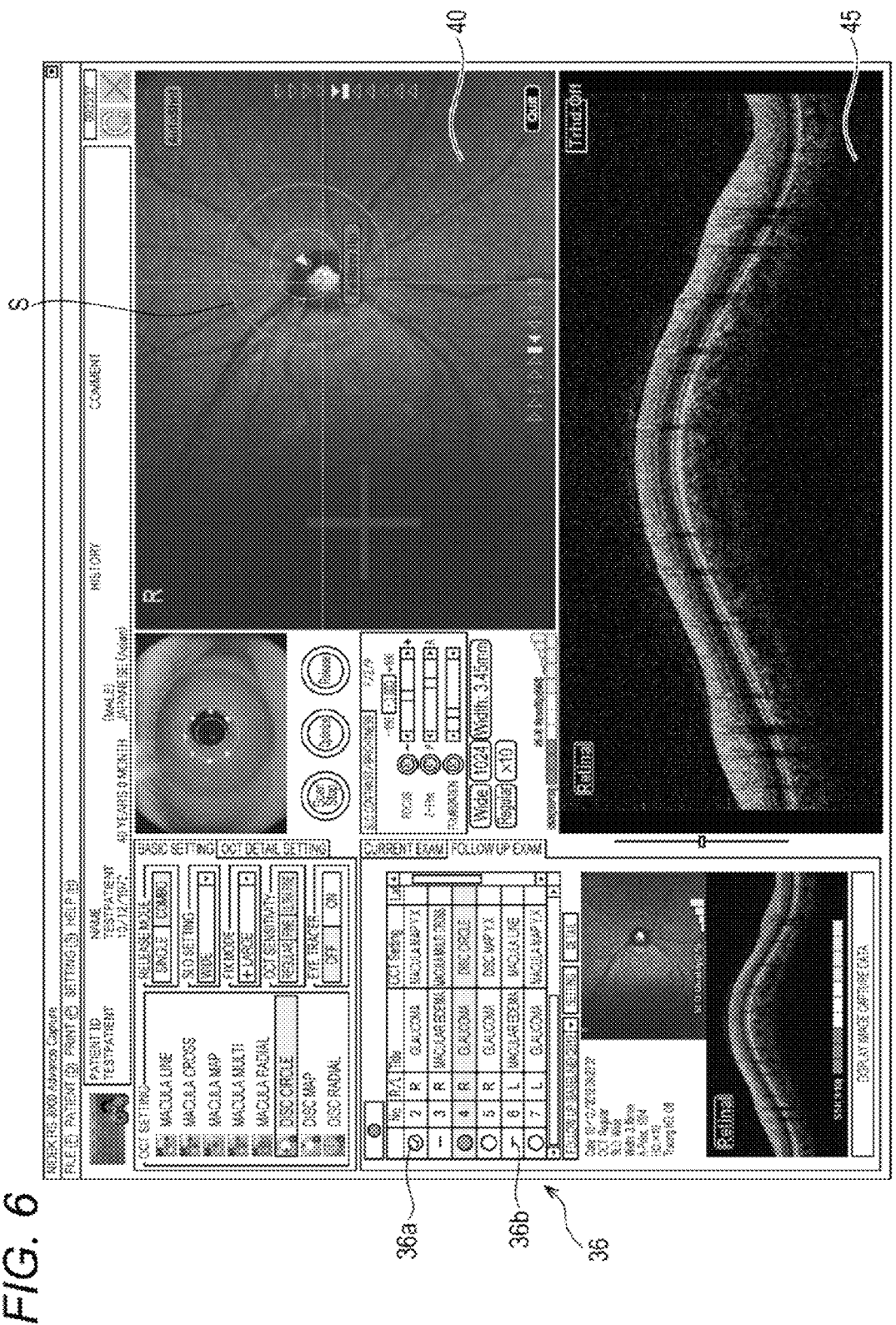
FIG. 6 is a diagram illustrating an exemplary image capture screen after setting of image capture data.

FIG. 6 is a diagram illustrating an exemplary image capture screen after the setting of the image capture data. The front image 40, the tomographic image 45, the scan line S, an image capture data list 36, and the like are displayed on the image capture screen. For example, all baselines are listed and displayed on the image capture data list 36 whether they are set as image capture data or not. Information such as the name of a tag attached to each baseline, and the photographing conditions of each baseline is displayed on each baseline. Consequently, the baselines can be identified.

Moreover, a mark 36a representing that it is set as image capture data is displayed for a baseline set as image capture data out of the baselines. For example, the mark 36a may be a circle, triangle, or the like (in the embodiment, the mark 36a is a circle). Moreover, a mark 36b representing that it is not set as image capture data is illustrated for a baseline that is not set as image capture data. The mark. 36b may be, for example, a horizontal line, a vertical line, or a slash. Naturally, the mark 36b may not be displayed for a baseline that is not set as image capture data and the corresponding portion, may be left blank.

If the examiner performs the alignment operation and operates the unillustrated photographing switch, the control unit 70 acquires the displayed front and tomographic images based on each baseline set as image capture data. For example, a baseline includes at least either of a captured image used as a template at the time of follow-up image capture or a photographing condition used to control the OCT optical system 100 at the time of follow-up image capture.

If image capture data contains a plurality of baselines, the control unit 70 sequentially uses the photographing conditions of the plurality of respective baselines as the photographing conditions of follow-up image capture. For example, the order of use of photographing conditions of the baselines may be, for example, the order set as the image capture data or an arbitrary order of image captures decided during the setting of the image capture data.

The control unit 70 performs template matching on a captured image using a captured image set as the baseline as a template. The control unit 70 controls the OCT optical system 100 based on the photographing condition of the baseline to perform image capture. The control of the OCT optical system 100 includes, for example, the control of the optical scanner 108 and the control of an unillustrated fixation target. At the time of image capture, for example, a target indicating that image capture is being performed is displayed in a field of a baseline during image capture in the image capture data list 36. The target indicating that image capture is being performed includes, for example, a change in the color, shape, or the like of the mark 36a and a change in the color of the field of a baseline for which image capture is being performed. If a plurality of baselines is set as image capture data, the control unit 70 may use a captured image of one baseline out of the plurality of baselines as a template. Alternatively, the control unit 70 may change the template on a baseline by baseline basis. Naturally, the control unit 70 may use as a template a captured image of a baseline arbitrarily set by the examiner, out of the plurality of baselines.

Moreover, for example, follow-up image capture with the set baseline may become difficult due to the large progression of a lesion. In such a case, the baseline of image capture data may be reset. The resetting of a baseline includes, for example, a change of the latest captured image to a new baseline (a new captured image). If the state of the examinee's eye changes very much, an image captured on the photographing condition of the baseline changes very much from the captured image of the template. As a consequence, the comparison between captured images (the comparison between a template and a captured image, which is described below) may become difficult. In such a case, the resettability of the baseline is useful. In other words, the baseline can be changed to the latest captured image. Hence, the possibility of successful follow-up image capture is increased. In other words, data set as image capture data for a follow-up is sot limited to a photographing condition. The data may be, for example, a captured image used as a template at the time of follow-up image capture.

If the image capture is completed on the photographing condition of one baseline, the control unit 70 controls the optical scanner on the photographing condition of the next baseline to perform image capture. The control unit 70 successively performs such control to change the photographing condition until image capture with all the baselines set as the image capture data is completed. Consequently, the control unit 70 performs follow-up image capture.

In the embodiment, the control unit 70 successively performs image captures until image capture is completed with all the baselines. The control unit 70 is not limited to this, but may stop image capture for each baseline. Alternatively, the control unit 70 may stop image capture when image capture with a predetermined number of baselines is completed. Moreover, the control unit 70 may be configured to be capable of stopping image capture by the operation of the examiner.

When image capture with the baselines is completed, the control unit 70 stores the acquired front and tomographic images as a baseline corresponding to the photographing condition upon acquisition. After the image capture, the examiner operates the operating unit 74 to return the display screen of the monitor 75 to the reference screen 80. The examiner selects each baseline to observe the front and tomographic images acquired on different dates on a baseline by baseline basis. For example, if the examiner selects one baseline, the front and tomographic images acquired on the photographing condition of the selected baseline are lined and displayed on the monitor 75. In other words, the front and tomographic images captured on a predetermined photographing condition on different dates are lined and displayed. Hence, the examiner can observe the progress by comparing these captured images.

As described above, in the embodiment, a plurality of baselines can be set as image capture data. Hence, follow-up image captures can be performed in a collective manner. Consequently, in the embodiment, the time and trouble of performing image captures one by one using each individual image capture data are reduced. Consequently, the burden on the examiner is reduced and the number of failures such as missed image capture at the time of follow-up image capture can be reduced. Moreover, the examiner can arbitrarily change the photographing condition upon observation of the progress. Hence, the examiner can arbitrarily add or delete a photographing condition (baseline). Consequently, the examiner can acquire sufficient information for a follow-up and promote efficiency in image capture.

<Modification>

The embodiment can also be applied to combo photographing. In the combo photographing, a plurality of image captures is successively performed on a predetermined photographing condition preset in accordance with the purpose of the image capture (for example, glaucoma, or age-related macular degeneration). For example, in the combo photographing, image captures may be successively performed in a plurality of scan patterns. In such a case, the control unit 70 sets the plurality of scan patterns used in the combo photographing as baselines in a collective manner. Naturally, the control unit 70 may select an arbitrary scan pattern desired by the examiner from the plurality of scan patterns and set the scan pattern as a baseline.

Moreover, the control unit 70 may set the plurality of scan patterns used in the combo photographing as baselines and subsequently set all the baselines automatically as image capture data. A baseline may be possible to be added and deleted after the setting of the image capture data. Consequently, a plurality of images captured can be set as baselines in a collective manner. Hence, the settings of baselines and image capture data become efficient and easy.

The control unit 70 may set a baseline for each image capture category by creating image capture categories (for example, glaucoma and macular disease) in the data of patients. In this case, if the examiner selects the image capture category, the control unit 70 extracts a baseline corresponding to the selected image capture category based on the name of the tab, and sets the baseline as image capture data. The method for setting a baseline to be extracted for each image capture category may be, for example, a method where the examiner presets a baseline for each image capture category. Naturally, a baseline is not necessarily preset for each image capture category. In this case, for example, when the examiner selects the image capture category, the control unit 70 may extract a baseline including the name of the image capture category based on the name of the tab of each baseline.

Moreover, the control unit 70 may notify the examiner of an optimal time for follow-up image capture according to the image capture category. For example, if the name of the image capture category is glaucoma, the control unit 70 displays on the monitor 75 information such as that image capture is to be performed, three months later. Moreover, if the control unit 70 calculates the optimal time for image capture according to the image capture category and the optimal time (diagnosis date) comes, the control unit 70 may display on the monitor 75 information indicating that image capture should be performed. Naturally, the control unit 70 may automatically extract the image capture category whose optimal time (diagnosis date) for image capture is today from the image capture categories. The control unit 70 may set a baseline of the extracted image capture category as image capture data. Consequently, it becomes possible to quickly set optimal image capture for the follow-up image capture of the day, which enables efficient image capture.

In the embodiment, the optical tomography apparatus that captures the fundus has been described as the ophthalmologic photographing apparatus. However, the present disclosure is not limited to this. The present disclosure can also be applied to an optical tomography apparatus that captures a tomographic image of the anterior segment.

In the embodiment, the control unit 70 may display a captured image of a baseline during follow-up image capture. Moreover, the control unit 70 may display on the monitor 75 the analysis result of the captured image of the baseline. The analysis result may be, for example, a layer detection result and/or the brightness intensity of the captured image.

In the embodiment, the control unit 70 sets image capture data for each of the left and right eyes. The embodiment is not limited to this, but the control unit 70 may set image capture data set for one of the eyes as image capture data of the other eye.

The present disclosure is not limited to the apparatus disclosed in the embodiment. For example, ophthalmologic photographing software (program) that performs the functions of the present apparatus (the control unit 70) illustrated in the embodiment may be provided to the system or apparatus via a network or various recording media. A computer (for example, a CPU) of the system or apparatus can also read and execute the program.

The ophthalmologic photography represented in the present embodiment can be performed not only by the present apparatus but also by another apparatus. Moreover, for example, software (program) for causing another computer to perform a process to be performed by the control unit 70 of the present apparatus can be supplied to a system or device via a network or various recording media. In this case, a computer (e.g., CPU or the like) of the system, or device reads the program to execute the process.

Moreover, in the embodiment, substantially all the processes in the present device may be controlled by the control unit 70. Moreover, a program (ophthalmologic program) for performing these processes may be recorded in a recording medium such as the memory 72. Furthermore, an information processing device (e.g., a computer) that can read the program may be used instead of the control unit 70.

In this configuration, an arithmetic unit (CPU or MPU) of the information processing device reads the program recorded in the recording medium and executes the processes. Therefore, it can be said that the program itself realizes the processes.

As the above information processing device, in addition to a general computer (e.g., a workstation or personal computer), a function expansion board or function expansion unit that is attached to a computer can be used.

Moreover, the above program includes program codes (an executable program, an intermediate code program, a source program, and the like) of software that realizes the processes. The program may be used singly or in combination with another program (such as an OS). Moreover, the program, may be read from a recording medium, then recorded once in memory (such as RAM) in the device, and subsequently read again to be executed.

Moreover, a recording medium in which the program is recorded may be one that can be separated readily from the information processing device, or one that is fixed (attached) to the device. Furthermore, a recording medium may be one that is connected to the device as an external storage device.

A magnetic tape such as a video tape or cassette tape, a magnetic disk such as a floppy (registered trademark) disk, MD, or hard, disk, a magneto-optical disk such as an MO, an optical disc such as a CD, DVD or BD, a memory card such as an IC card or optical card, a semiconductor memory such as a Mask ROM, EPROM, EEPROM, flash ROM, or USB memory, or the like can be applied as such a recording medium.

Moreover, a recording medium that is connected, to the information processing device via networks (an intranet, the Internet, and the like) can be used. In this case, the information processing device acquires the program by downloading via a network. In other words, the above program may be acquired via a transmission medium (a medium holding the program in flux) such as a network (one that is connected to a wired or wireless channel). It is preferable that a program for download should previously be stored in the information processing device (or in a transmitting side device/receiving side device). Moreover, the above recording medium is a non-transitory (non-transitory) medium.

If image captures are sequentially performed in a plurality of scan patterns as combo photographing, the plurality of scan patterns in which image captures were performed in the combo photographing is set as baselines in a collective manner. With such a configuration, a plurality of image captures can be set as baselines in a collective manner, which makes the settings of the baselines and image capture data efficient and easy.

The target display 36a set as image capture data may be displayed for a baseline set as image capture data out of the baselines. For example, the target display 36a may be expressed in a display such as a circle or a triangle. Moreover, the target display 36b that is not set as image capture data may be displayed for a baseline that is not set as the image capture data. For example, the target display 36b includes a display such as a horizontal line, a vertical line, or a slash. Naturally, the configuration to leave the field blank without displaying the target display 36b can also be cited.

If the examiner performs the alignment operation and operates the unillustrated photographing switch, the control unit 70 may acquire the displayed front and tomographic images based on each baseline set as image capture data. For example, a baseline includes at least either a captured image used as a template at the time of follow-up image capture or a photographing condition used to control the OCT optical system 100 at the time of the follow-up image capture. If image capture data is set with a plurality of baselines, the control unit 70 may sequentially perform image captures under the photographing conditions of the baselines set as the image capture data. For example, the order of baselines with which image capture is performed includes the configuration such as to perform image capture in the order set as image capture data or to set the order of image captures arbitrarily during the setting of image capture data and perform image captures on the set order.

Moreover, it may be configured to be possible to reset a baseline of image capture data in the setting of a template if follow-up image capture with the set baseline becomes difficult, for example, due to the large progression of a lesion. For example, the configuration to change the latest captured image to a new baseline (new captured image) can be cited. Such a configuration is useful if the state of the examinee's eye changes very much and, upon the setting of the photographing condition of a baseline, a captured image to be a reference of the setting may change very much, and therefore it becomes difficult to make a comparison between captured images (a comparison between a template and a captured image, which is described below). In other words, the latest captured image can be changed to a new baseline (new captured image), and the possibility of successful follow-up image capture is then increased. In other words, data set as image capture data for a follow-up is not limited to a photographing condition, but may be a captured image used as a template at the time of follow-up image capture.

For example, if image captures are sequentially and successively performed in a plurality of scan patterns as combo photographing, the plurality of scan patterns in which image capture was performed in the combo photographing is set as baselines in a collective manner. Naturally, only an arbitrary scan pattern of the examiner may be selected from the plurality of scan patterns and set as a baseline. Moreover, the plurality of scan patterns used in the combo photographing may be set as baselines to subsequently set all the baselines captured in the combo photographing automatically as image capture data. It may be configured to be possible to add and delete a baseline after the setting of image capture data. These configurations enable the collective setting of a plurality of image captures as baselines, and the settings of baselines and image capture data become efficient and easy.

Moreover, if the optimal time for image capture is calculated according to the image capture category and the optimal time (the time required based on the diagnosis of the day) comes, a notification indicating that image capture should be performed may be displayed. Naturally, it may be configured such that the image capture category whose optimal time for image capture is that day is extracted automatically from the image capture categories and a baseline of the extracted image capture category is set as image capture data. Such a configuration enables the quick setting of only image capture necessary for the follow-up image capture of the day, and image capture can be performed efficiently.

The ophthalmologic, photographing apparatus of the present disclosure may be the following first to sixth, ophthalmologic photographing apparatuses. Moreover, the ophthalmologic photographing program of the present disclosure may be the following first ophthalmologic photographing program.

The first ophthalmologic photographing apparatus includes a photographing optical system having an optical scanner configured to scan light emitted from a light source over an examinee's eye and a detector configured to detect a coherent state of reflected light of measurement light from the examinee's eye, the measurement light having been emitted from the light source, and reference light, the photographing optical system being configured to capture a tomographic image of the examinee's eye in response to an output signal from the detector, a reference data setting unit configured to set, as reference data for a follow-up, the photographing conditions of at least one or more captured images previously acquired by the ophthalmologic photographing apparatus, an image capture data setting unit configured to set the reference data as image capture data for the follow-up from at least one or more reference data set by the reference data setting unit in order to perform follow-up image capture in accordance with progress, and a controller configured to control the photographing optical system based on the reference data set as the image capture data and acquire a tomographic image of the examinee's eye.

In the second ophthalmologic photographing apparatus according to the first ophthalmologic photographing apparatus, the image capture data setting unit sets the image capture data where a plurality of the reference data is combined from the at least one or more set reference data, and the controller controls the photographing optical system based on a photographing condition of each of the plurality of reference data set as the image capture data, and successively acquires tomographic images of the fundus of the examinee's eye under respective photographing conditions of the plurality of reference data.

In the third ophthalmologic photographing apparatus according to the first ophthalmologic photographing apparatus, if the reference data is at least either added to or deleted from the image capture data after the setting of the image capture data, the image capture data setting unit resets the image capture data.

The fourth ophthalmologic photographing apparatus according to the first ophthalmologic photographing apparatus includes a display controller configured to display the reference data set by the reference data setting unit on a display unit, in which the reference data setting unit sets a captured image, a photographing condition of the captured image, and accompanying information that can identify (recognize) the captured image and that is set by the operation of an operating unit, as the reference data from the at least one or more captured images previously acquired by the ophthalmologic photographing apparatus, and the display controller displays the accompanying information corresponding to the captured image, as well as the captured image, on a setting screen, for setting the image capture data.

In the fifth ophthalmologic photographing apparatus according to the first ophthalmologic photographing apparatus, the captured images previously acquired by the ophthalmologic photographing apparatus are captured images successively captured by the ophthalmologic photographing apparatus on a plurality of different photographing conditions, and the reference data setting unit sets the captured image and the photographing condition of the captured image as reference data in a collective manner.

In the sixth, ophthalmologic photographing apparatus according to the first ophthalmologic photographing apparatus, the photographing conditions include at least any information of a scan pattern, scan position information, optimization information, and fixation position information.

The first ophthalmologic photographing program is an ophthalmologic photographing program to be executed in a control apparatus that controls the operation of an ophthalmologic photographing apparatus including a photographing optical system having an optical scanner configured to scan light emitted from a light source over an examinee's eye and a detector configured to detect a coherent state of reflected light of measurement light from the examinee's eye, the measurement light, having been emitted from a light source, and reference light, the photographing optical system being configured to capture a tomographic image of the examinee's eye in response to an output signal from the detector, and the ophthalmologic photographing program is executed by a processor of the control apparatus to cause the control apparatus to execute a reference data setting step of setting a photographing condition of a captured image previously acquired by the ophthalmologic photographing apparatus that captures a tomographic image of the examinee's eye as reference data for a follow-up, an image capture data setting step of setting the reference data as image capture data for the follow-up from at least one or more reference data set in the reference data setting step, and a control step of controlling the ophthalmologic photographing apparatus based on the reference data set as the image capture data in the image capture data setting step, and acquiring a tomographic image.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmologic photographing apparatus comprising:
    a photographing optical system including an optical scanner configured to scan an examinee's eye with measurement light and a detector configured to detect a coherent state of reflected light of the measurement light from the examinee's eye and reference light, the photographing optical system being configured to capture a tomographic image of the examinee's eye in response to an output signal from the detector;
    a reference data setting unit configured to set a plurality of reference data for a follow-up, each of the plurality of reference data comprising each of photographing conditions of each of previously acquired captured images of the examinee's eye;
    an image capture data setting unit configured to select and combine two or more of the plurality of reference data set by the reference data setting unit to generate image capture data that comprises the selected two or more of the plurality of reference data and set the image capture data for the follow up; and
    a tomographic image acquisition controller configured to acquire a plurality of tomographic images of the examinee's eye by controlling the photographing optical system based on the image capture data in a collective manner under the each of the photographing conditions included in the image capture.

2. The ophthalmologic photographing apparatus according to claim 1, wherein the image capture data setting unit at least either adds the reference data to the image capture data or deletes the reference data from the image capture data after the setting of the image capture data to reset the image capture data.

3. The ophthalmologic photographing apparatus according to claim 1, further comprising a display controller configured to display the reference data set by the reference data setting unit on a display unit, wherein
    the each of the plurality of reference data further comprises a previously acquired captured image and accompanying information with which the captured image is identifiable and that is set by operation of an operating unit, and
    the display controller displays the captured image and the accompanying information corresponding to the captured image on a screen for setting the image capture data.

4. The ophthalmologic photographing apparatus according to claim 3, wherein the display controller displays the accompanying information with a name displayed on a tag assigned to the reference data.

5. The ophthalmologic photographing apparatus according to claim 1, wherein
    the previously acquired captured images are captured images successively captured on a plurality of different photographing conditions, and
    the reference data setting unit sets the captured image and a photographing condition of the captured image as reference data.

6. The ophthalmologic photographing apparatus according to claim 1, wherein the photographing conditions include at least any of a scan pattern, scan position information, optimization information, and fixation position information.

7. An ophthalmologic photographing method comprising:
    setting a plurality of reference data for a follow-up, each of the plurality of reference data comprising each of photographing conditions of each of previously acquired tomographic images of an examinee's eye;
    selecting and combining two or more of the plurality of reference data;
    generating image capture data that comprises the selected two or more of the plurality of reference data;
    setting the image capture data for the follow up; and acquiring a plurality of tomographic images of the examinee's eye based on the image capture data in a collective manner under the each of the photographing conditions included in the image capture.

8. A recording medium where an ophthalmologic photographing program is recorded, wherein
the ophthalmologic photographing program causes an information processing apparatus to execute the ophthalmologic photographing method according to claim 7, the information processing apparatus controlling operation of an ophthalmologic photographing apparatus comprising a photographing optical system including an optical scanner configured to scan an examinee's eye with measurement light and a detector configured to detect a coherent state of reflected light of the measurement light from the examinee's eye and reference light, the photographing optical system being configured to capture a tomographic image of the examinee's eye in response to an output signal from the detector.

9. The ophthalmologic photographing apparatus according to claim 1, wherein each said photographing condition included in the each of the plurality of reference data is the photographing condition of respectively different said previously acquired captured image.

10. The ophthalmologic photographing method according to claim 7, wherein each said photographing condition included in the each of the plurality of reference data is the photographing condition of respectively different said previously acquired tomographic image.

11. The ophthalmologic photographing apparatus according to claim 1, further comprising a list on which all of the plurality of reference data are listed, the list comprising marks representing that the two or more of the plurality of reference data are selected and included in the image capture data.

12. The ophthalmologic photographing method according to claim 7, further comprising making a list on which all of the plurality of reference data are listed, and making in the list marks representing that the two or more of the plurality of reference data are selected and included in the image capture data.

13. The ophthalmologic photographing apparatus according to claim 1, wherein
the image capture data setting unit deletes one reference data from the image capture data, or
the image capture data setting unit adds one reference data which is not selected and not included in the image capture data to the image capture data.

14. The ophthalmologic photographing method according to claim 7, further comprising:
deleting one reference data from the image capture data, or
adding one reference data which is not selected and not included in the image capture data to the image capture data.

15. The ophthalmologic photographing apparatus according to claim 1, wherein the tomographic image acquisition controller acquires the plurality of tomographic images in the collective manner in a predetermined order of either an order in which the two or more of the plurality of reference data are set as the image capture data by the image capture data setting unit or an arbitrary order decided during the setting of the image capture data by the image capture data setting unit.

16. The ophthalmologic photographing method according to claim 7, wherein the method comprises acquiring the plurality of tomographic images in the collective manner in a predetermined order of either an order in which the two or more of the plurality of reference data are set as the image capture data by the image capture data setting unit or an arbitrary order decided during the setting of the image capture data by the image capture data setting unit.

17. The ophthalmologic photographing apparatus according to claim 1, wherein the each of the plurality of reference data further comprises the each of the previously acquired captured images of the examinee's eye.

18. The ophthalmologic photographing method according to claim 7, wherein the each of the plurality of reference data further comprises the each of the previously acquired captured images of the examinee's eye.

19. The ophthalmologic photographing apparatus according to claim 1, further comprising a list on which all of the plurality of reference data are listed, wherein the list comprises:
marks representing that the two or more of the plurality of reference data are selected and included in the image capture data; and
a cell representing that the reference data of the cell is not selected and not included in the image capture data.

20. The ophthalmologic photographing method according to claim 7, further comprising:
making a list on which all of the plurality of reference data are listed, wherein the list comprises:
making in the list marks representing that the two or more of the plurality of reference data are selected and included in the image capture data; and
making in the list a cell representing that the reference data of the cell is not selected and not included in the image capture data.

* * * * *